United States Patent [19]

Desai et al.

[11] Patent Number: 5,502,175

[45] Date of Patent: Mar. 26, 1996

[54] FATTY ACID ESTERS OF METHYLGLUCOSIDE DERIVATIVES

[75] Inventors: Natvarlei Desai, Dinslaken; Klaus Wisotzki, Kamp-Lintfort, both of Germany

[73] Assignee: Th. Goldschmidt AG, Germany

[21] Appl. No.: 230,928

[22] Filed: Apr. 21, 1994

[30] Foreign Application Priority Data

Apr. 22, 1993 [DE] Germany .............. 43 13 117.4

[51] Int. Cl.$^6$ .............. C07H 15/04; C07H 15/06; C07H 15/08

[52] U.S. Cl. .............. 536/18.3; 536/115; 536/116

[58] Field of Search .............. 536/115, 18.3, 536/116

[56] References Cited

U.S. PATENT DOCUMENTS

| | | | |
|---|---|---|---|
| 4,898,934 | 2/1990 | Lueders et al. | 536/18.6 |
| 5,246,695 | 9/1993 | Hintz et al. | 424/70 |

FOREIGN PATENT DOCUMENTS

| | | |
|---|---|---|
| 0432646 | 12/1989 | European Pat. Off. |
| 0415636 | 3/1991 | European Pat. Off. |
| 0507004 | 10/1992 | European Pat. Off. |

OTHER PUBLICATIONS

Zhang et al., *Riyong Huaxue Gongye*, vol. 5, pp. 221–225 (1991).

*Primary Examiner*—Jeffrey Mullis
*Attorney, Agent, or Firm*—Banner & Allegretti, Ltd.

[57] ABSTRACT

Fatty acid esters of methylglucoside derivatives of formula I

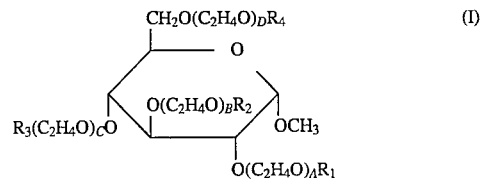

wherein A, B, C, D=21 to 75, $R_1$, $R_2$, $R_3$, $R_4$=H or

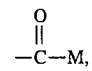

with $R_1$–$R_4$ not simultaneously being H, and M=$C_{11}$–$C_{18}$ alkenyl or alkyl.

8 Claims, No Drawings

FATTY ACID ESTERS OF METHYLGLUCOSIDE DERIVATIVES

FIELD OF THE INVENTION

This invention is directed to fatty acid esters of methylglucoside derivatives, a process for their preparation and use.

DESCRIPTION OF THE RELATED ART

Glucose and saccharose derivatives may be recovered from renewable raw materials. Therefore, interest in utilizing such chemicals has grown worldwide. This is associated with the fact that the starting materials, due to agricultural over-production, are low in cost and available in unlimited amounts.

By methylation of glucose, methylglucoside is prepared which has good thermal stability in comparison to saccharose. The methylglucoside has an α- and a β-form. Furthermore, starch and cellulose may also be employed in the production of methylglucoside.

In the production of fatty acid esters of methylglucoside derivatives according to hitherto common processes, considerable drawbacks appear because the carbohydrates are thermally unstable. Therefore, such reactions frequently give rise to caramelization and hence, brown coloration of the products, so that application in the cosmetic field is no longer possible. In addition, expensive purification of these products is necessary, rendering the entire process less economic. Another problem is insufficient solubility of the substance in non-toxic solvents which also may find application in the cosmetic field.

F. H. Otey et al., J. Am. Oil Chem. Soc., Vol. 38, p. 517ff, October 1961, describe the preparation of fatty acid esters of methylglucoside ether. Therein, one proceeds in such fashion that initially, the methylglucoside is ethoxylated using ethylene oxide in amounts of from 5 to 20 moles at temperatures of about 160° to 175° C. The products are amber-colored and have viscosities of from 21,000 to 800 cP. Subsequently, the products are esterified using sodium hydroxide and xylene as the solvent. Thereafter, purification of the obtained product is effected to remove traces of xylene from the reaction product.

U.S. Pat. No. 4,687,843 describes esterified methylglucoside compounds propoxylated with from 5 to 50 moles of propylene oxide, which are obtained by reaction of a propoxylated methylglucoside with a fatty acid at elevated temperature in the presence of an acid catalyst. The products are used as moisturizers in skin protecting formulations. These products are merely emulsifiers which, due to their low solubility in water, are unsuitable for aqueous formulations such as shampoos and foam baths. Furthermore, these products do not have viscosity-improving properties.

U.S. Pat. No. 4,268,498 describes the use of polyoxyethylene (17 to 23) glucose fatty acid esters as base material in cosmetic sticks.

EP-0 432 646 A2 describes alkoxyalkylglucosides linked with quaternary ether groups. They are cation-active nitrogen-containing compounds which consequently are able to form nitrosamines.

U.S. Pat. No. 5/059,443 describes low-ethoxylated alkylglucosides intended to be used in low-caloric, fat-containing food formulations. They are poorly soluble in water and do not have viscosity-improving properties.

SUMMARY AND DESCRIPTION OF THE PREFERRED EMBODIMENTS

The technical problem solved by the present invention is the providing of new nitrogen-free, non-ionogenic fatty acid esters of methylglucoside derivatives which are present in substantially purer form than the other methylglucoside derivatives known in the prior art and thus, are better suited for use in cosmetic formulations such as shampoos and foam baths.

The technical problem is solved by fatty acid esters of methylglucoside derivatives of formula I

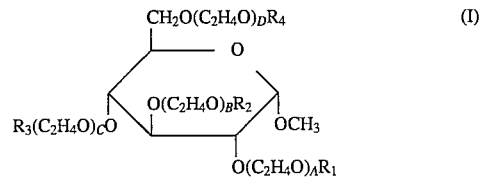

wherein A, B, C, D=21 to 75, $R_1$, $R_2$, $R_3$, $R_4$=H or

with $R_1$–$R_4$ not simultaneously being H, and M=$C_{11}$–$C_{18}$ alkenyl or alkyl.

In a preferred embodiment, $R_1$, $R_4$=

and $R_2$, $R_3$=H, or $R_1$=

and $R_2$, $R_3$, $R_4$=H, or $R_4$=

and $R_1$, $R_2$, $R_3$=H In a particularly preferred embodiment, M=$C_{17}$ alkenyl.

The fatty acid esters of the invention are prepared by ethoxylating methylglucoside with from 84 to 300 moles, preferably 120 moles of ethylene oxide. Subsequently, esterification is effected with from 2 to 4 moles, preferably from 1.8 to 3.5 moles of a saturated or unsaturated neat $C_{11}$–$C_{18}$ fatty acid using acid catalysts.

Preferably, as the fatty acids, there are used oleic acid, stearic acid, linoleic acid, linolenic acid, lauric acid, or a mixture of same.

As the acid catalyst, there may be used sulfuric acid, hydrochloric acid, phosphoric acid, p-toluenesulfonic acid, methanesulfonic acid, ethanesulfonic acid, boron trifluoride as well as other organic or inorganic acids.

Esterification is effected without solvent at temperatures of between 110° and 150° C. at normal pressure and preferably, in vacuum at from 50 to 150 mbars and from 80° to 100° C.

By the process according to the invention, fatty acid esters are obtained which are recovered as light-colored products. Decomposition or caramelization are not determined.

Surprisingly, it was also determined that in contrast to the initially esterified and in the second reaction step ethoxylated fatty acid esters, the fatty acid esters prepared according to the invention have considerably improved viscosity in various surfactant systems.

Thus, the products prepared according to the invention permit optimum viscosity adjustment of bathing and shampoo preparations at relatively low dosage.

TABLE 1

| Surfactant mixtures | Wt.-% | Comparative Example (Viscosity in mPa · s) | Ex. 1 | Ex. 2 |
|---|---|---|---|---|
| Product | 2.5 | 18,000 | 24,600 | 25,200 |
| Sodium laurylether-sulfate (30%) | 9.0 | | | |
| Cocamidopropyl-betaine (30%) | 3.0 | | | |
| Water | 85.5 | | | |
| Product | 4.0 | 38,000 | 52,700 | 52,500 |
| Disodium laurylether-sulfosuccinate (32%) | 12.0 | | | |
| Water | 44.0 | | | |
| Product | 4.0 | 40,800 | 58,900 | 57,700 |
| Sodium laurylether-sulfate (30%) | 12.0 | | | |
| Water | 84.0 | | | |
| Product | 4.0 | 17,680 | 25,500 | 26,400 |
| Cocoamphocarboxy-glycinate (40%) | 12.0 | | | |
| Water | 84.0 | | | |

All viscosity measurements conducted at 25° C.

The fatty acid esters of the invention are used as thickeners for surfactant-containing solutions in cosmetic formulations.

However, the fatty acid esters prepared according to the invention not only act as thickening agents in surfactant-containing formulations but, in addition, they have a very good moisturizing effect and reduce irritation values of common ingredients such as, e.g., anionic and non-ionic surfactants in shampoo and bathing preparations.

The following Examples explain the invention in greater detail.

EXAMPLES

Comparative Example

In a 1 l three-necked flask with a vacuum-sealed stirring system, controllable temperature measuring unit and descending cooler with coolable collector, 508.5 g (1.8 moles) of oleic acid is esterified with 194.1 g (1.0 mole) of methylglucoside and 1.5 g of potassium carbonate at 180° C. under a 100 mbar vacuum within three hours. Here, 662.5 g of α-D-methylglucoside dioleate is obtained as a light-yellow oil having the following characteristic data:

| Saponification number: | 137 |
|---|---|
| Acid number: | 7 |
| pH Value (5% MeOH/water): | 7.5 |

Ethoxylation

To 500 g (0,967 moles) of α-D-methylglucoside dioleate, 2 g of NaOH is added and ethoxylated with 5105.75 g (116.04 moles) of ethylene oxide at 140° C. according to known procedures. The ethoxylated α-D-methylglucoside dioleate ester has the following characteristic data:

| Saponification number: | 14 |
|---|---|
| Acid number: | 1 |
| Water content: | 0.19% |
| Color (Gadner): | 2 |

Example 1

In a 1 l three-necked flask with a vacuum-sealed stirring system, controllable temperature measuring unit and descending cooler with coolable collector, 547.4 g (0.1 moles) of polyoxyethylene-120 methylglucoside, 50.85 g (0.18 moles) of oleic acid, and 2.0 g of sulfuric acid are reacted under reduced pressure of 100 mbars at 140° C. within 5 hours. Following the reaction period, the product is neutralized with 5 g of (50%) NaOH, and 580 g of a light-yellow is obtained having the following characteristic numbers:

| Saponification number: | 17 |
|---|---|
| Acid number: | 1 |
| Hydroxyl number: | 22 |
| pH Value (5% MeOH/water): | 6.5 |

Example 2

According to Example 1, 56.5 g (0.2 moles) of oleic acid is reacted with 547.4 g (0.1 moles) of polyoxyethylene-120 methylglucoside, and 2.0 g of p-toluenesulfonic acid within 5 hours, wherein 583 g of a light-yellow reaction product is obtained having the following characteristic numbers:

| Saponification number: | 19 |
|---|---|
| Acid number: | 2 |
| Hydroxyl number: | 20 |
| pH Value (5% MeOH/water): | 6.2 |

The viscosity behavior of the products produced according to Examples 1 and 2 was tested in various surfactant mixtures. These results as well as viscosities of the Comparative Example are represented in Table 1.

Examples 3 and 4

| Baby Shampoo | | |
|---|---|---|
| | Wt.-% | |
| | 3 | 4 |
| Sodium laurylethersulfate (28%) | 35.0 | 35.0 |
| Cocoamphocarboxyglycinate (40%) | 8,0 | — |
| Cocamidopropylbetaine (30%) | — | 7.0 |
| Product according to Example 1 | 2.5 | — |
| Product according to Example 2 | — | 2.5 |
| Preserving agent | 0.1 | 0.1 |
| Water | 54.4 | 55.4 |
| | 100.0 | 100.0 |

Example 5

| Shampoo (as a gel) | Wt.-% |
|---|---|
| Sodium laurylethersulfate (30%) | 36.0 |
| Cocamidopropylbetaine (30%) | 20.0 |
| GRILLOCAM E 20 (Methyl Gluceth-20) | 4.0 |
| Product according to Example 2 | 3.5 |
| Preserving agent | 0.1 |
| Water | 36.4 |
|  | 100.0 |

What is claimed is:

1. A mixture of fatty acid esters of methylglucoside derivatives of formula I

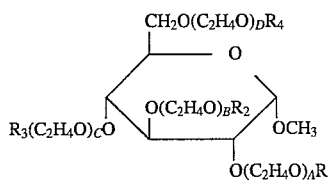

wherein A, B, C, D=21 to 75, $R_1$, $R_2$, $R_3$, $R_4$=H or

with $R_1$–$R_4$ not simultaneously being H, and M= $C_{11}$–$C_{18}$ alkenyl or alkyl.

2. The fatty acid esters according to claim 1, characterized in that contains a methylglucoside wherein

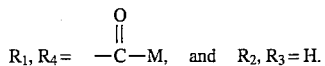

$R_1, R_4 =$ —C—M, and $R_2, R_3 =$ H.

3. The fatty acid esters according to claim 2, characterized in that the mixture contains a methylglucoside wherein M=$C_{17}$ alkenyl.

4. The fatty acid esters according to claim 1, characterized in that contains a methylglucoside wherein

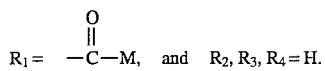

$R_1 =$ —C—M, and $R_2, R_3, R_4 =$ H.

5. The fatty acid esters according to claim 4, characterized in that the mixture contains a methylglucoside wherein M=$C_{17}$ alkenyl.

6. The fatty acid esters according to claim 1, characterized in that contains a methylglucoside wherein

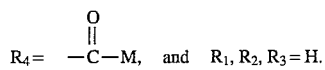

$R_4 =$ —C—M, and $R_1, R_2, R_3 =$ H.

7. The fatty acid esters according to claim 6, characterized in that the mixture contains a methylglucoside wherein M=$C_{17}$ alkenyl.

8. The fatty acid esters according to claim 1, characterized in that contains a methylglucoside wherein M=$C_{17}$ alkenyl.

* * * * *